United States Patent
Xiao et al.

(10) Patent No.: US 10,151,852 B2
(45) Date of Patent: *Dec. 11, 2018

(54) MULTI-AZIMUTH NUCLEAR MAGNETIC RESONANCE LOGGING INSTRUMENT AND ANTENNA EXCITATION METHOD

(71) Applicant: CHINA UNIVERSITY OF PETROLEUM-BEIJING, Beijing (CN)

(72) Inventors: Lizhi Xiao, Beijing (CN); Guangzhi Liao, Beijing (CN); Xin Li, Beijing (CN); Feng Deng, Beijing (CN); Sihui Luo, Beijing (CN); Zhe Sun, Beijing (CN); Wei Liu, Beijing (CN); Weiliang Chen, Beijing (CN); Jie Wang, Beijing (CN)

(73) Assignee: CHINA UNIVERSITY OF PETROLEUM-BEIJING, Beijing (CN)

( * ) Notice: Subject to any disclaimer, the term of this patent is extended or adjusted under 35 U.S.C. 154(b) by 232 days.

This patent is subject to a terminal disclaimer.

(21) Appl. No.: 15/258,843

(22) Filed: Sep. 7, 2016

(65) Prior Publication Data

US 2017/0082775 A1 Mar. 23, 2017

(30) Foreign Application Priority Data

Sep. 23, 2015 (CN) .......................... 2015 1 0614128

(51) Int. Cl.
*G01V 3/32* (2006.01)
*G01V 3/14* (2006.01)
(Continued)

(52) U.S. Cl.
CPC .............. *G01V 3/32* (2013.01); *G01N 24/081* (2013.01); *G01R 33/3415* (2013.01); *G01R 33/383* (2013.01); *G01R 33/3808* (2013.01)

(58) Field of Classification Search
CPC .............. G01R 33/3808; G01R 33/341; G01R 33/3415; G01R 33/383; G01R 33/445; G01V 3/32; G01N 24/081
See application file for complete search history.

(56) References Cited

U.S. PATENT DOCUMENTS

2003/0210050 A1    11/2003  Prammer et al. ............. 324/315
2004/0130324 A1*   7/2004   Edwards .............. G01N 24/081
                                                       324/303
(Continued)

FOREIGN PATENT DOCUMENTS

CN      101098047 A      1/2008
CN      102519999 A      6/2012
(Continued)

OTHER PUBLICATIONS

English translation of CN 102519999A provided by Google Patents.*
The Chinese First Examination Report of corresponding Chinese patent application No. 201510614128.1, dated Jul. 27, 2017.

*Primary Examiner* — Rishi Patel
(74) *Attorney, Agent, or Firm* — J.C. Patents

(57) ABSTRACT

The present invention provides a multi-azimuth nuclear magnetic resonance logging instrument and an antenna excitation method, the nuclear magnetic resonance logging instrument includes: a probe framework and a shielding layer arranged in the probe framework; a plurality of main magnets are provided above and below the shielding layer, respectively; central axes of the main magnets are parallel with each other, and distances between the central axes of each of the main magnets and a central axis of the probe (Continued)

framework are the same; a distance between central axes of any two main magnets is not smaller than a first preset value; and an antenna is provided at outer side of each main magnet, and a plurality of the antennas are fed independently. In the present invention, circumferential recognizing capability of the nuclear magnetic resonance logging instrument can be improved and three-dimensional (radial, axial and circumferential) stratum detection can be achieved.

9 Claims, 4 Drawing Sheets

(51) Int. Cl.
*E21B 47/024* (2006.01)
*G01R 33/34* (2006.01)
*G01N 24/08* (2006.01)
*G01R 33/3415* (2006.01)
*G01R 33/38* (2006.01)
*G01R 33/383* (2006.01)

(56) References Cited

U.S. PATENT DOCUMENTS

| | | | |
|---|---|---|---|
| 2008/0174309 A1 | 7/2008 | Pusiol et al. | 324/306 |
| 2016/0291191 A1* | 10/2016 | Fukushima | G01R 33/3415 |

FOREIGN PATENT DOCUMENTS

| | | |
|---|---|---|
| CN | 203594440 U | 5/2014 |
| CN | 203867568 U | 10/2014 |

* cited by examiner

MULTI-AZIMUTH NUCLEAR MAGNETIC RESONANCE LOGGING INSTRUMENT AND ANTENNA EXCITATION METHOD

CROSS-REFERENCE TO RELATED APPLICATIONS

This application claims priority to Chinese Patent Application No. 201510614128.1, filed on Sep. 23, 2015, the content of which is hereby incorporated by reference in its entirety.

TECHNICAL FIELD

The present invention relates to the technical field of nuclear magnetic resonance logging, and more particularly to a nuclear magnetic resonance logging instrument and an antenna excitation method.

BACKGROUND

The phenomenon of nuclear magnetic resonance (Nuclear Magnetic Resonance, NMR) has been applied in various fields, such as physics, chemistry, material science, life science and medical science and the like, shortly after it was discovered in 1946. In 1950s, the nuclear magnetic resonance came into use in the oil and gas industry, and initially applied in the field of oil reservoir rock physics. A nuclear magnetic resonance logging instrument can utilize the nuclear magnetic resonance principle to detect stratum information around the borehole, and have unique capabilities of qualitative recognition and quantitative evaluation for the reservoir fluid.

A probe is one of the important parts in the nuclear magnetic resonance logging instrument, and the structure of the probe determines key performances, such as a measuring mode of the instrument, a nuclear magnetic resonance region and nuclear magnetic resonance signal intensity. The probe of nuclear magnetic resonance logging instrument mainly includes a magnet and an antenna, the magnet can form a static magnetic field for polarizing spinning hydrogen protons, and the antenna can emit a radio frequency field for turning the spinning hydrogen protons, after the radio frequency field is removed, the spinning hydrogen protons start to precess along the static magnetic field, thus generate nuclear magnetic resonance inductive signals, and the stratum conditions can be analyzed by detecting the nuclear magnetic resonance inductive signals.

The existing nuclear magnetic resonance logging instrument usually adopts a column-shaped magnet, rounded sides of the magnet are an N pole and an S pole, respectively, the magnetic field distribution is formed by closed magnetic lines of force pointing from the N pole to the S pole, the antenna surrounds the magnet, and can excite polarized stratum regions all around (360 degrees) the borehole, so that there is no detecting blind zone around the borehole, multi-frequency multi-slice measurement can be performed, but the measure signal is only an average signal of signals in the 360-degree stratum. Accordingly, the nuclear magnetic resonance logging instrument in the prior art only can perform signal detection at a radial depth dimension and an axial depth dimension, but have no capability to detect signals in the circumferential multi-azimuth sensitive area.

SUMMARY

The present invention provides a nuclear magnetic resonance logging instrument and an antenna excitation method, so as to solve the technical problems that the nuclear magnetic resonance logging instrument in the prior art only can perform signal detection at a radial depth dimension and an axial depth dimension, but have no capability to detect signals in the circumferential multi-azimuth sensitive area.

The present invention provides a nuclear magnetic resonance logging instrument, including: a probe and a control device; wherein the probe is electrically connected to the control device;

the probe is configured to polarize hydrogen protons in the stratum, and transmit nuclear magnetic resonance signals generated by the hydrogen protons to the control device;

the control device is configured to receive nuclear magnetic resonance signals transmitted by the probe, and analyze stratum information according to the nuclear magnetic resonance signals;

wherein the probe includes: a probe framework and a shielding layer arranged in the probe framework;

a plurality of main magnets are provided above and below the shielding layer, respectively;

central axes of the main magnets are parallel with each other, and distances between the central axis of each of the main magnets and a central axis of the probe framework are the same;

a distance between central axes of any two main magnets is not smaller than a first preset value;

an antenna is provided at outer side of each main magnet, and a plurality of the antennas are fed independently.

Furthermore, four main magnets are uniformly provided above and below the shielding layer, respectively, eight main magnets are uniformly distributed along a circumference of the probe framework, and the main magnets above the shielding layer are arranged in a staggered manner with the main magnets below the shielding layer;

the main magnet has a triangular prism shape, and upper and lower end surfaces thereof are both of isosceles right-angled triangle shape, the upper and lower end surfaces are parallel with each other, and are perpendicular to the central axis of the main magnet;

a plane where a central axis of the probe framework and the central axis of the main magnet lie in is a first plane, the first plane is perpendicular to the right-angled side of the end surface of the main magnet;

the main magnet is magnetized radially.

Furthermore, an auxiliary magnet is provided corresponding to two right-angled sides of the end surface of the main magnet, respectively, a distance between the auxiliary magnet and corresponding right-angled side is not greater than a second preset value;

the auxiliary magnet has a quadrangular prism shape, and has an equal height with the main magnet, and two long sides of the end surface of the auxiliary magnet are parallel to the two right-angled sides of the main magnet, respectively;

the auxiliary magnet is magnetized in the extending direction of the long side of the end surface, and the main magnet and the auxiliary magnet are magnetized in opposite directions.

Furthermore, the main magnet and the auxiliary magnet are fixed to the shielding layer by an adhesive.

Furthermore, the antenna is formed by winding a deoxidized copper sheet, and has a square loop shape or a mosquito coil shape.

Furthermore, the antenna comprises an N-turns deoxidized copper sheet, a distance between the first turn and the second turn is equal to a distance between the (N−1)-th turn and the N-th turn, and a distance between the k-th turn and the (k+1)-th turn is greater than that of the first turn and the second turn;

both k and N are natural numbers, 2<k<N−1, N>3.

Furthermore, the probe framework is provided with multiple grooves, a plurality of the antennas are fixed within the grooves, respectively, and the groove is filled with highly magnetic permeable materials.

Furthermore, the nuclear magnetic resonance logging instrument also includes: an antenna excitation device configured to feed the antenna;

the antenna excitation device includes a plurality of excitation channels, a plurality of the antennas are electrically connected to the plurality of excitation channels, respectively.

Furthermore, the probe framework is provided with a through hole, a central axis of the through hole coincides with the central axis of the probe framework;

a support frame penetrates through the through hole, and is fixedly connected to a housing of the probe, or a diversion pipe through which drilling fluid is circulated penetrates through the through hole, and the diversion pipe is fixedly connected to the probe framework via a metal piece.

The present invention also provides an antenna excitation method based on any of the nuclear magnetic resonance logging instrument described above, comprising:

exciting one antenna to achieve a downhole mono-azimuth angle detection;

exciting at least two antennas to achieve a downhole multi-azimuth angle detection; or exciting all the antennas to achieve a downhole omni-directional detection.

In the nuclear magnetic resonance logging instrument and the antenna excitation method provided in the present invention, upper and lower layers of main magnets are provided in the probe framework, independently fed antennas are all provided at outer side of the main magnets, stratum information detection at different azimuth angles can be achieved by exciting different antennas, so that circumferential recognizing capability of the nuclear magnetic resonance logging instrument can be improved and three-dimensional (radial, axial and circumferential) stratum detection can be achieved. Besides, upper and lower layers of main magnets can achieve detection at different azimuth angles, respectively, so that the circumferential recognizing capability of the probe can be increased without increasing a radial dimension of the probe, thus costs can be saved and downhole detection cannot be affected.

DESCRIPTION OF REFERENCE SIGNS

Figure 1:
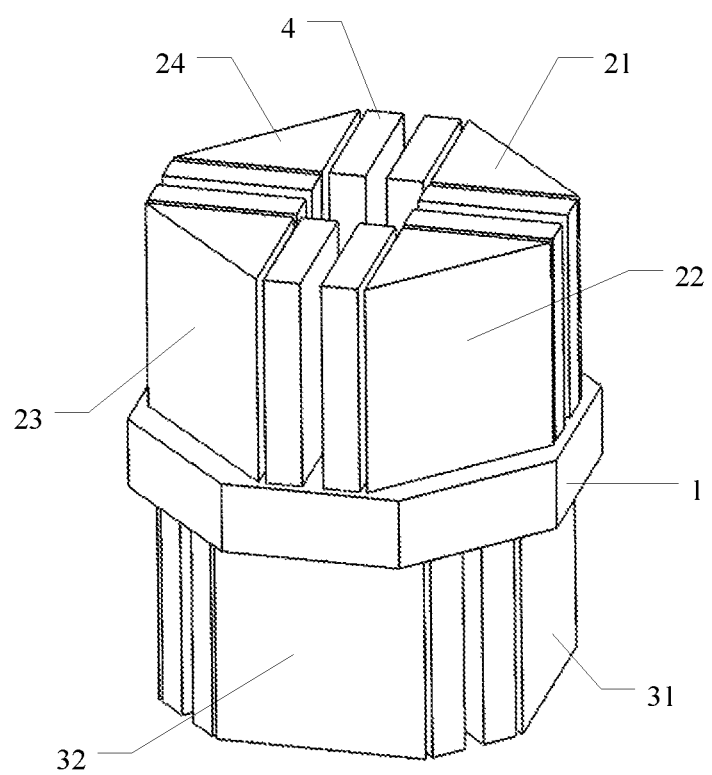
FIG. 1 is a structural schematic diagram of a main magnet and a shielding layer in a nuclear magnetic resonance logging instrument according to Embodiment 1 of the present invention.

| | | |
|---|---|---|
| 1-Shielding layer | 21-Eastern magnet | 22-Southern magnet |
| 23-Western magnet | 24-Northern magnet | 31-Southeastern magnet |
| 32-Southwestern magnet | 4-Auxiliary magnet | 5-Square loop antenna |
| 6-Mosquito coil antenna | | |

DESCRIPTION OF EMBODIMENTS

In order to make the objects, technical solutions, and advantages of the embodiments of the present invention clearer, the technical solutions in the embodiments of the present invention are hereinafter described clearly and completely with reference to the accompanying drawings in the embodiments of the present invention. Obviously, the embodiments described here are part of the embodiments of the present invention and not all of the embodiments. All other embodiments obtained by persons skilled in the art on the basis of the embodiments of the present invention without any creative efforts all fall within the scope of the invention.

Embodiment 1

Embodiment 1 of the present invention provides a nuclear magnetic resonance logging instrument. The nuclear magnetic resonance logging instrument in this embodiment can include: a probe and a control device; wherein the probe is electrically connected to the control device;

the probe is used to polarize hydrogen protons in the stratum, and transmit nuclear magnetic resonance signals generated by the hydrogen protons to the control device;

the control device is used to receive nuclear magnetic resonance signals transmitted by the probe, and analyze stratum information according to the nuclear magnetic resonance signals;

wherein the probe includes: a probe framework and a shielding layer 1 arranged in the probe framework;

a plurality of main magnets are provided above and below the shielding layer 1, respectively;

central axes of the main magnets are parallel with each other, and distances between the central axes of each of the main magnets and a central axis of the probe framework are the same;

a distance between central axes of any two main magnets is not smaller than a first preset value;

an antenna is provided at outer side of each main magnet, and a plurality of the antennas are fed independently.

Particularly, the specific implementation method to analyze stratum information according to the nuclear magnetic resonance signals by the control device belongs to the prior art, and therefore no more details are given in this embodiment.

The probe framework in this embodiment can have a columnar structure, and can be provided with a receiving chamber, the shielding layer 1 and the main magnet are fixed therein. The main magnets are divided into upper and lower layers, which are provided above and below the shielding layer, respectively; the shielding layer 1 can be made from highly magnetic permeable materials, thus avoiding mutual interference of the magnetic fields generated by the upper and lower layers of main magnets, and the main magnet can be fixed to the shielding layer 1 via an adhesive.

The main magnet can have a columnar structure or a pyramid structure, and the like. In particular, the columnar structure can have a shape of a cylinder or a prism. In this embodiment, the central axis of the columnar structure refers to a straight line where a connecting line between central points on the upper and lower end surfaces lies in, while the central axis of the pyramid structure refers to a straight line where a connecting line between a vertex and a central point on the lower end surface lies in. Of course, the main magnet also can be other shapes, as long as a static magnetic field that used for exciting hydrogen protons in the stratum can be generated.

FIG. 1 is a structural schematic diagram of a main magnet and a shielding layer 1 in a nuclear magnetic resonance logging instrument according to Embodiment 1 of the present invention. As shown in FIG. 1, four main magnets are uniformly provided above and below the shielding layer 1, respectively, of course, the number of the main magnets is not limited to eight, but based on the actual requirements persons skilled in the art can increase or reduce the number of the main magnets accordingly. The Embodiment only uses eight main magnets as an example to illustrate the present invention.

For illustrative purposes, the eight main magnets can be named according to the compass bearing: four magnets above the shielding layer 1 are an eastern magnet 21, a southern magnet 22, a western magnet 23 and a northern magnet 24 in sequence, and four magnets below the shielding layer 1 are a southeastern magnet 31, a southwestern magnet 32, a northwestern magnet and a northeastern (the northwestern magnet and the northeastern are not shown in the figure).

Particularly, central axes of the main magnets are parallel with each other, and distances between the central axes of each of the main magnets and a central axis of the probe framework are the same, so as to guarantee that the distances between each of the main magnets and a central axis of the probe framework are substantially equal, as such, intensities of the magnetic fields generated by each main magnet at the same downhole radial depth are also substantially equal, so as to facilitate stratum information detection.

Besides, a distance between central axes of any two main magnets is not smaller than a first preset value, that is to say, the main magnets above the shielding layer 1 do not coincide with the main magnets below the shielding layer 1, as such, eight detection areas are formed along a circumference of the probe framework, and thus the circumferential detection recognizing capability of the probe can be increased. The first preset value can be determined by sizes of the probe and the main magnet, generally speaking, the first preset value can be between 1 to 5 mm.

An antenna is provided at outer side of each main magnet, and a plurality of the antennas are fed independently. In this embodiment, the number of the main magnets can be eight, accordingly, the number of the antennas also can be eight, and the eight antennas are provided at outer side of the eight main magnets, respectively. The probe framework is provided with eight grooves, eight antennas are fixed within the corresponding grooves, respectively, and the groove also can be filled with highly magnetic permeable materials, which can improve the antenna efficiency and guarantee a depth of the sensitive area.

In the practical work, after the probe enters the well, the static magnetic fields generated by a plurality of main magnets will circumferentially excite the hydrogen protons at different azimuth angles, when there is a need to detect stratum information at a certain azimuth angle, excitation signals can be transmitted to the antenna corresponding to the azimuth angle, the radio frequency field generated by the antenna can turn the hydrogen protons, after the excitation signals are not transmitted to the antenna any longer, the hydrogen protons will precess along the static magnetic field to generate nuclear magnetic resonance inductive signals, and the stratum conditions at mono-azimuth angle can be obtained correspondingly by detecting the nuclear magnetic resonance inductive signals. Similarly, at least two antennas can be excited to achieve a downhole multi-azimuth angle detection, and all the antennas can be excited to achieve a downhole omni-directional detection.

During the downhole detection, stratum information at different axial depths can be detected by lifting or lowering the probe; stratum information at different radial depths can be detected by changing an excitation frequency of the antenna; and stratum information at different azimuth angles can be detected by exciting different antennas. Therefore, a three-dimensional detection capability of the probe can be achieved by combining signals at an axial depth dimension, a radial depth dimension and a circumferential azimuth angle. In this embodiment, the axial direction refers to an extending direction of the central axis of the well, the radial direction refers to an extending direction of the well center along the radius, and the circumferential direction refers to an extending direction around the well center.

In the nuclear magnetic resonance logging instrument provided in this embodiment, upper and lower layers of main magnets are provided in the probe framework, independently fed antennas are all provided at outer side of the main magnets, stratum information detection at different azimuth angles can be achieved by exciting different antennas, so that circumferential recognizing capability of the nuclear magnetic resonance logging instrument can be improved and three-dimensional (radial, axial and circumferential) stratum detection can be achieved. Besides, upper and lower layers of main magnets can achieve detection at different azimuth angles, respectively, so that the circumferential recognizing capability of the probe can be increased without increasing a radial dimension of the probe, thus costs can be saved and downhole detection cannot be affected.

Furthermore, the main magnets above the shielding layer 1 are arranged in a staggered manner with the main magnets below the shielding layer. As shown in FIG. 1, the southeastern magnet 31 on the lower layer is provided between the eastern magnet 21 and southern magnet 22 on the upper layer, and the southwestern magnet 32 on the lower layer is provided between the southern magnet 22 and the western magnet 23 on the upper layer. Moreover, eight main magnets are uniformly distributed along a circumference of the probe framework, that is, in multiple central axes corresponding to multiple magnets, each central axis is staggered at an angle of 45° with the adjacent central axis along a circumference of the probe framework.

Figure 2:
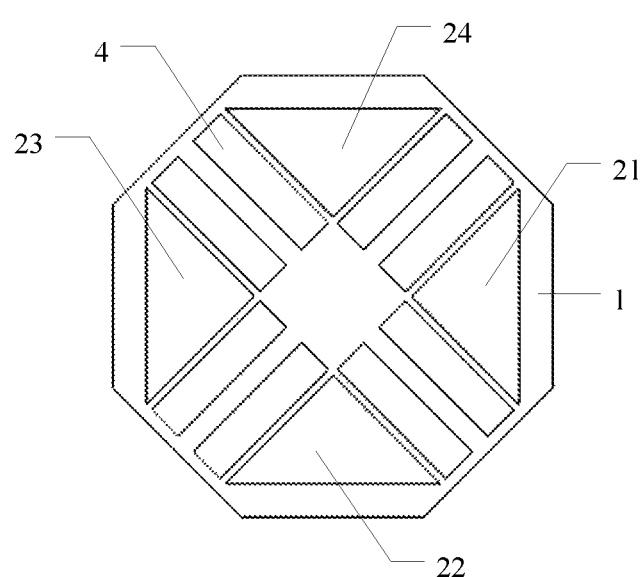
FIG. 2 is a top view of the main magnet in FIG. 1.

The four main magnets above the shielding layer 1 can be uniformly arranged, and the four main magnets below the shielding layer 1 also can be uniformly arranged. FIG. 2 is a top view of the main magnet in FIG. 1. As shown in FIG. 2, the eastern magnet 21, the southern magnet 22, the western magnet 23 and the northern magnet 24 are uniformly arranged, and distances between each main magnet and an adjacent main magnet are the same.

The main magnet in this embodiment can have a triangular prism shape, and upper and lower end surfaces thereof are both of isosceles right-angled triangle shape; for each main magnet, a plane where a central axis of the probe framework and a central axis of the main magnet lie in is a first plane, the first plane is perpendicular to the right-angled side of the end surface of the main magnet. The main magnet is magnetized radially, from inside to outside, or vice versa, besides, all the main magnets are magnetized in the same direction, that is, magnetized all from inside to outside, or vice versa.

In this embodiment, the main magnets above the shielding layer 1 can be arranged in a staggered manner with the main magnets below the shielding layer, each main magnet can create a sensitive area range of 45°, and downhole stratum information at different azimuth angles can be detected by exciting antennas corresponding to different main magnets. Table 1 shows detection results obtained by exciting different antennas in this embodiment.

TABLE 1

| Mode | Excited antenna | Sensitive area |
| --- | --- | --- |
| 1 | Antenna corresponding to the eastern magnet 21 | 45° in the East |
| 2 | Antenna corresponding to the southern magnet 22 | 45° in the South |
| 3 | Antenna corresponding to the western magnet 23 | 45° in the West |
| 4 | Antenna corresponding to the northern magnet 24 | 45° in the North |
| 5 | Antenna corresponding to the southeastern magnet 31 | 45° in the Southeast |
| 6 | Antenna corresponding to the southwestern magnet 32 | 45° in the Southwest |
| 7 | Antenna corresponding to the northwestern magnet | 45° in the Northwest |
| 8 | Antenna corresponding to the northeastern magnet | 45° in the Northeast |

As can be seen from Table 1, stratum information at different azimuth angles can be detected by exciting different antennas, so that the nuclear magnetic resonance logging instrument can have a circumferential recognizing capability.

On the basis of the technical solutions in the above embodiments, it is preferable that an auxiliary magnet 4 that having focusing effect can be arranged beside a right-angled side of the main magnet. As shown in FIG. 1 and FIG. 2, an auxiliary magnet 4 is provided corresponding to two right-angled sides of the end surface of the main magnet, respectively, the auxiliary magnet 4 can have a quadrangular prism shape, and can be fixed to the shielding layer 1 by an adhesive. The auxiliary magnet 4 has an equal height with the main magnet, and two long sides at the end surface of the auxiliary magnet 4 are parallel to the two right-angled sides of the main magnet, respectively.

Two auxiliary magnets 4 corresponding to each main magnet are both arranged near the corresponding right-angled side of the main magnet, that is, a distance between the auxiliary magnet 4 and the corresponding right-angled side should be smaller than a distance between the auxiliary magnet 4 and a tilted side of the end surface of the main magnet. Besides, in order to achieve a better focusing effect, a distance between the auxiliary magnet 4 and corresponding right-angled side is not greater than a second preset value. The second preset value can be determined by sizes of the main magnet and the auxiliary magnet 4, for example, the second preset value can be 5 mm.

The auxiliary magnet 4 is magnetized in the extending direction of the long side of the end surface, in order to achieve a focusing effect, and the main magnet and the auxiliary magnet 4 can be magnetized in opposite directions, if the main magnet is magnetized from inside to outside, then the auxiliary magnet 4 is magnetized from outside to inside; if the main magnet is magnetized from outside to inside, then the auxiliary magnet 4 is magnetized from inside to outside.

In this embodiment, auxiliary magnets 4 are arranged at both sides of the main magnet, and the auxiliary magnet 4 and the main magnet are magnetized in opposite directions, so as to adjust the static magnetic field generated by the main magnet, make intensity of the static magnetic field at the same radial depth and different azimuth angles more uniform, and improve a performance of the nuclear magnetic resonance logging instrument.

Figure 3:
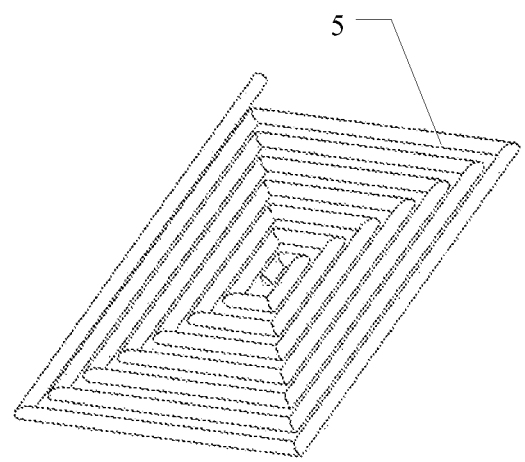
FIG. 3 is a structural schematic diagram of a square loop antenna in a nuclear magnetic resonance logging instrument according to Embodiment 1 of the present invention.
Figure 4:
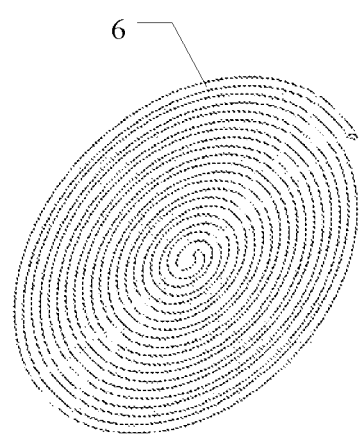
FIG. 4 is a structural schematic diagram of a mosquito coil antenna in a nuclear magnetic resonance logging instrument according to Embodiment 1 of the present invention.
Figure 5:
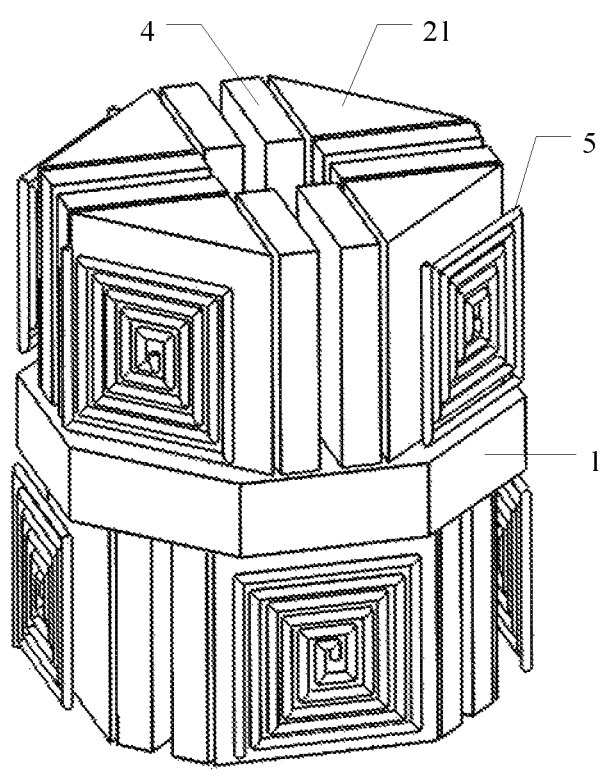
FIG. 5 is a schematic diagram illustrating positions of a square loop antenna and a main magnet in a nuclear magnetic resonance logging instrument according to Embodiment 1 of the present invention.

On the basis of the technical solutions in the above embodiments, it is preferable that the antenna is formed by winding a deoxidized copper sheet, and has a square loop shape or a mosquito coil shape. FIG. 3 is a structural schematic diagram of a square loop antenna in a nuclear magnetic resonance logging instrument according to Embodiment 1 of the present invention. FIG. 4 is a structural schematic diagram of a mosquito coil antenna in a nuclear magnetic resonance logging instrument according to Embodiment 1 of the present invention. FIG. 5 is a schematic diagram illustrating positions of a square loop antenna and a main magnet in a nuclear magnetic resonance logging instrument according to Embodiment 1 of the present invention.

As shown in FIG. 5, a plurality of square loop antennas 5 are provided at outer side of the plurality of main magnets, respectively, when the antenna is a mosquito coil antenna 6, the positions of the mosquito coil antenna 6 and the main magnet are similar thereto. In the radio frequency fields generated by the square loop antenna 5 and the mosquito coil antenna 6, magnetic lines of force are denser, an orthogonality between the magnetic lines of force and a plane where the antenna is located is better, which is favorable for orthogonal match between the radio frequency field and the static magnetic field, and can further improve the performance of nuclear magnetic resonance logging instrument.

On the basis of the technical solutions in the above embodiments, it is preferable that the antenna comprises an N-turns deoxidized copper sheet, a distance between the first turn and the second turn is equal to a distance between the (N−1)-th turn and the N-th turn, and a distance between the k-th turn and the (k+1)-th turn is greater than that of the first turn and the second turn; both k and N are natural numbers, 1<k<N−1, N>3.

When the antenna is fed, a position at the center of the antenna radius has higher magnetic field intensity. For example, when the antenna includes ten-turns coils, the magnetic field intensity outside the fourth turn to the seventh turn coils is higher, while the magnetic field intensity outside the first turn and the tenth turn coils is lower, and the radio frequency fields generated by the antennas can be more uniform by arranging the middle turn coils of the antenna sparsely, and arranging the innermost and the outermost coils densely.

Furthermore, the nuclear magnetic resonance logging instrument in this embodiment also includes: an antenna excitation device for feeding the antenna; the antenna excitation device includes a plurality of excitation channels, a plurality of the antennas are electrically connected to the plurality of excitation channels, respectively. A sensitive area slice at different azimuth angles can be generated by providing excitation signals to different antennas.

On the basis of the technical solutions in the above embodiments, it is preferable that the probe framework is provided with a through hole, a central axis of the through hole coincides with the central axis of the probe framework.

In terms of a cable-type nuclear magnetic resonance logging instrument, a support frame can penetrate through a through hole, and be fixedly connected to a housing of the probe, so as to provide a mechanical support for the probe; in terms of a nuclear magnetic resonance logging-while-drilling instrument, a diversion pipe through which drilling fluid is circulated can penetrate through the through hole, and the diversion pipe is fixedly connected to the probe framework via a metal piece, so as to extract drilling fluid generated during drilling operations outside the well timely.

Embodiment 2

Embodiment 2 of the present invention provides an antenna excitation method based on the nuclear magnetic resonance logging instrument according to any of the above embodiments. The antenna excitation method in this embodiment can include:

exciting one antenna to achieve a downhole mono-azimuth angle detection;

exciting at least two antennas to achieve a downhole multi-azimuth angle detection;

exciting all the antennas to achieve a downhole omni-directional detection.

Principles for exciting an antenna in this embodiment is similar to that in Embodiment 1, and therefore no more details are given herein.

In the antenna excitation method provided in this embodiment, stratum information detection at different azimuth angles can be achieved by exciting different antennas, so that circumferential recognizing capability of the nuclear magnetic resonance logging instrument can be improved and three-dimensional (radial, axial and circumferential) stratum detection can be achieved. Besides, upper and lower layers of main magnets can achieve detection at different azimuth angles, respectively, so that the circumferential recognizing capability of the probe can be increased without increasing a radial dimension of the probe, thus costs can be saved and downhole detection cannot be affected.

Finally, it should be noted that the above embodiments are merely provided for describing the technical solutions of the present invention, but not intended to limit the present invention. It should be understood by persons skilled in the art that although the present invention has been described in detail with reference to the foregoing embodiments, modifications can be made to the technical solutions described in the foregoing embodiments, or equivalent replacements can be made to partial or all technical features in the technical solutions; however, such modifications or replacements do not cause the essence of corresponding technical solutions to depart from the scope of the embodiments of the present invention.

What is claimed is:

1. A nuclear magnetic resonance logging instrument, comprising: a probe and a control device; wherein the probe is electrically connected to the control device; wherein the probe is configured to polarize hydrogen protons in the stratum, and transmit nuclear magnetic resonance signals generated by the hydrogen protons to the control device;

the control device is configured to receive nuclear magnetic resonance signals transmitted by the probe, and analyze stratum information according to the nuclear magnetic resonance signals;

the probe comprises: a probe framework and a shielding layer arranged in the probe framework; a plurality of main magnets are provided above and below the shielding layer, respectively;

central axes of the main magnets are parallel with each other, and distances between the central axis of each of the main magnets and a central axis of the probe framework are the same;

a distance between central axes of any two main magnets is not smaller than a first preset value;

an antenna is provided at outer side of each main magnet, and a plurality of the antennas are fed independently;

eight main magnets are uniformly distributed along a circumference of the probe framework, where four main magnets are uniformly provided above the shielding layer, and four main magnets are uniformly provided below the shielding layer, and the four main magnets above the shielding layer are arranged in a staggered manner with the four main magnets below the shielding layer;

each of the eight main magnets has a triangular prism shape, and upper and lower end surfaces thereof are both of isosceles right-angled triangle shape;

a plane where the central axis of the probe framework and the central axis of each of the main magnets lie in is a first plane, the first plane is perpendicular to right-angled sides of the upper and lower end surfaces of each of the main magnets;

the main magnet is magnetized radially.

2. The nuclear magnetic resonance logging instrument according to claim 1, wherein: an auxiliary magnet is provided corresponding to each of two right-angled sides of an end surface of each main magnet, a distance between the auxiliary magnet and corresponding right-angled side is not greater than a second preset value;

the auxiliary magnet has a quadrangular prism shape, and has an equal height with corresponding main magnet, and two long sides of an end surface of the auxiliary magnet are parallel to corresponding right-angled side of the corresponding main magnet;

the auxiliary magnet is magnetized in an extending direction of the two long sides of the end surface, and the auxiliary magnet and the corresponding main magnet are magnetized in opposite directions.

3. The nuclear magnetic resonance logging instrument according to claim 2, wherein: each of the main magnets and the auxiliary magnet are fixed to the shielding layer by an adhesive.

4. The nuclear magnetic resonance logging instrument according to claim 1, wherein: each of the plurality of the antennas is formed by winding a deoxidized copper sheet, and has a square loop shape or a coiled snake shape.

5. The nuclear magnetic resonance logging instrument according to claim 4, wherein: each of the plurality of the antennas comprises an N-turns deoxidized copper sheet, a distance between the first turn and the second turn is equal to a distance between the (N−1)-th turn and the N-th turn, and a distance between the k-th turn and the (k+1)-th turn is greater than that of the first turn and the second turn;

both k and N are natural numbers, $2<k<N-1$, $N>4$.

6. The nuclear magnetic resonance logging instrument according to claim 1, wherein:

the probe framework is provided with multiple grooves, the plurality of the antennas are fixed within the grooves, respectively, and the grooves are filled with highly magnetic permeable materials.

7. The nuclear magnetic resonance logging instrument according to claim 1, further comprising: an antenna excitation device configured to feed the plurality of the antennas;

the antenna excitation device includes a plurality of excitation channels, the plurality of the antennas are electrically connected to the plurality of excitation channels, respectively.

8. The nuclear magnetic resonance logging instrument according claim 1, wherein, the probe framework is provided with a through hole, a central axis of the through hole coincides with the central axis of the probe framework;

a support frame penetrates through the through hole, and is fixedly connected to a housing of the probe, or a diversion pipe through which drilling fluid is circulated penetrates through the through hole, and the diversion pipe is fixedly connected to the probe framework via a metal piece.

9. An antenna excitation method based on the nuclear magnetic resonance logging instrument according to claim 1, comprising:

exciting one antenna to achieve a downhole mono-azimuth angle detection;

exciting at least two antennas to achieve a downhole multi-azimuth angle detection; or exciting all the antennas to achieve a downhole omni-directional detection.

\* \* \* \* \*